United States Patent
Bosch et al.

(10) Patent No.: US 12,021,340 B2
(45) Date of Patent: Jun. 25, 2024

(54) CONTACT APPARATUS AND MEDICAL DEVICE

(71) Applicant: Siemens Healthcare GmbH, Erlangen (DE)

(72) Inventors: Christian Bruno Bosch, Fürth (DE); Florian Fleischmann, Eggolsheim (DE); Norbert Scherer, Pinzberg (DE)

(73) Assignee: Siemens Healthineers AG, Forchheim (DE)

( * ) Notice: Subject to any disclaimer, the term of this patent is extended or adjusted under 35 U.S.C. 154(b) by 415 days.

(21) Appl. No.: 17/381,179

(22) Filed: Jul. 20, 2021

(65) Prior Publication Data
US 2022/0029314 A1  Jan. 27, 2022

(30) Foreign Application Priority Data

Jul. 21, 2020  (DE) ...................... 10 2020 209 168.4

(51) Int. Cl.
*A61B 6/00* (2006.01)
*H01R 4/48* (2006.01)

(52) U.S. Cl.
CPC ............ *H01R 4/489* (2013.01); *A61B 6/4405* (2013.01); *A61B 6/4441* (2013.01)

(58) Field of Classification Search
CPC ................................. A61B 6/56; A61B 6/4405
See application file for complete search history.

(56) References Cited

U.S. PATENT DOCUMENTS

| | | | |
|---|---|---|---|
| 6,031,185 A * | 2/2000 | Bouveret | H01R 4/646 439/98 |
| 10,898,060 B2 | 1/2021 | Yamada et al. | |
| 2012/0289821 A1* | 11/2012 | Graumann | A61B 6/4441 378/19 |
| 2017/0077688 A1 | 3/2017 | Metzler | |

FOREIGN PATENT DOCUMENTS

| | | |
|---|---|---|
| CN | 1192063 A | 9/1998 |
| CN | 106463925 A | 2/2017 |
| WO | 2014072258 A1 | 5/2014 |

OTHER PUBLICATIONS

German Office Action for German Application No. 10 2020 209 168.4 dated Apr. 22, 2021.

* cited by examiner

*Primary Examiner* — Dani Fox
(74) *Attorney, Agent, or Firm* — Lempia Summerfield Katz LLC

(57) ABSTRACT

A contact apparatus having at least one conductive, elastic, structured contact unit that may assume a first state and a second state and may be brought by supplying energy, such as pressure, from the first state into the second state, is provided for a particularly rapid and simple electrical contacting with a ground potential of cable shields of electrical cables with different diameters. The contact unit is configured so that, in the first state, the contract unit has a preparation for detachably inserting a plurality of electrical cables, and that, in the second state, the contract unit fixes the cables and establishes an electrical contact with the cable shields of the cables.

18 Claims, 5 Drawing Sheets

CONTACT APPARATUS AND MEDICAL DEVICE

This application claims the benefit of German Patent Application No. DE 10 2020 209 168.4, filed on Jul. 21, 2020, which is hereby incorporated by reference in its entirety.

BACKGROUND

The present embodiments relate to a contact apparatus for electrical contacting for electrical cables with a cable shield.

To contact a cable shield of an electrical cable and to establish a connection with a ground potential of a conductive housing of an electrical or electronic device or a counterpart provided separately in order to derive interference and compensation currents, it is typical to remove insulation of the cable along a section and to fasten the exposed cable shield on a housing part (e.g., shield sheet). This is generally carried out by electrically conductive fastening elements such as cable clamps, cable terminals, screw terminals, spring sheets, or shield clamping saddles. In addition, the cables are frequently fixed with cable ties in order to prevent the cable shield from sliding and becoming damaged. If a plurality of cables, for example, of an assembly is present, each one is to be introduced and fixed individually into the fastening element, for example. If the cables also have different diameters, the contacting is frequently inadequate, or an adjusted fastening element is to be used for each cable.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a possibility for easily and rapidly contacting cable shields of a number of electrical cables with a ground potential of a housing of an electrical device is provided. As another example, a suitable medical device is provided.

The contact apparatus of one or more of the present embodiments for electrically contacting cable shields of electrical cables with a ground potential has at least one conductive, elastic, structured contact unit that may assume a first state and a second state, and may be brought from the first state into the second state by supplying energy. The contact unit is configured so that, in the first state, the contact unit has a preparation for detachably inserting a plurality of electrical cables, and that in the second state, the contact unit fixes the cables and establishes an electrical contact with the cable shields of the cables. By the contact unit, which may be brought rapidly from the first state into the second state if necessary, a number of cables with different diameters may simultaneously be electrically contacted with the ground potential (e.g., the housing of a device or similar). This may be easily carried out by the cables in the first state of the contact unit being inserted into the contact unit in the region of the exposed cable shields and in the second state being fastened in the contact unit and contacted. Different diameters of various cables also no longer play a role as a result of the elasticity of the contact unit since the contact unit may adjust itself automatically. Manufacturing costs and service costs may be reduced by rapidly inserting the cables.

According to one embodiment, the exertion of pressure onto the conductive, elastic, structured contact unit causes the contact unit to move from the first state to the second state. The application of pressure may be carried out particularly quickly and easily. Therefore, pressure may be exerted onto the contact unit by a pressure element, for example.

In one embodiment, for a simple assembly and rapid exchange of cables, the conductive, elastic, structured contact unit moves from the second state into the first state when the pressure is taken away.

According to a further embodiment, the conductive, elastic, structured contact unit is formed from a conductive rubber or elastomer. Conductive rubbers or elastomers of this type are known and may be manufactured in any forms. A particularly large bandwidth of cable diameters may be fixed simultaneously by the elasticity of the corresponding materials.

According to a further embodiment, the conductive, structured contact unit has at least one element that has cutouts and webs. For example, the elements may have one (e.g., three-dimensional) mesh-type structure. In the non-compressed state (e.g., first state), one such mesh-type structure may have a plurality of webs and cutouts, for example, where in the second, compressed state, the webs are close to one another or even pressed against one another, and in this process, the cutouts are reduced in size.

According to a further embodiment, the conductive, structured contact unit has at least two elements that are arranged so that the at least two elements are at a distance from one another in the first state and in the second state, are close to one another or in contact with one another. If, for example, two or more elements of this type are arranged at a distance adjacent to one another in a columnar manner, in the first state, the cables may be inserted through the cutouts or between the spacings and in the second state, the fixing and contacting may be carried out by pressure.

For example, the contact unit, in the second state, connects the cable shields electrically with the ground potential of the corresponding electrical device to which the cable shields are assigned.

According to a further embodiment, the contact apparatus has a frame or a structure with a pressure element (e.g., a plate) embodied to exert pressure onto the contact unit. If the pressure element is pressed onto the contact unit, the cables are fixed and contacted. In this state, the contact unit may be fixed (e.g., by tightly screwing or clamping the pressure element). Similarly, the pressure may be taken away again by releasing the screws or clamps, for example, and thus, the contact unit may be transferred back into the first state so that the cables may be removed again.

The present embodiments also include a medical device having an afore-described contact apparatus. The medical device is, for example, embodied as a mobile x-ray device with a C-arm for holding an x-ray detector and an x-ray source, where the cables are embodied to supply power to components of the C-arm.

DETAILED DESCRIPTION

Figure 1:
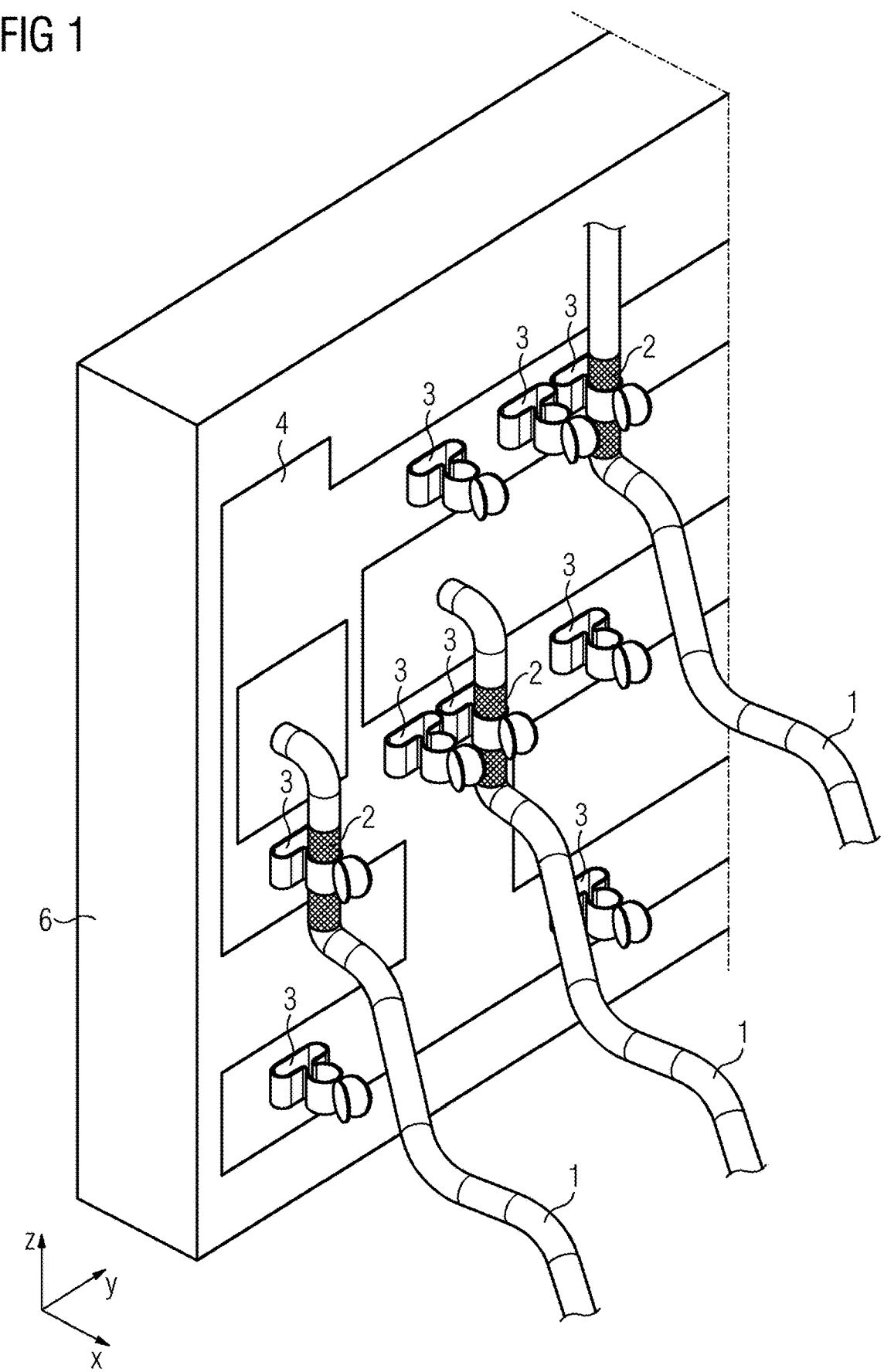
FIG. 1 shows a perspective top view of a known shield with spring sheets for contacting cable shields.
Figure 2:
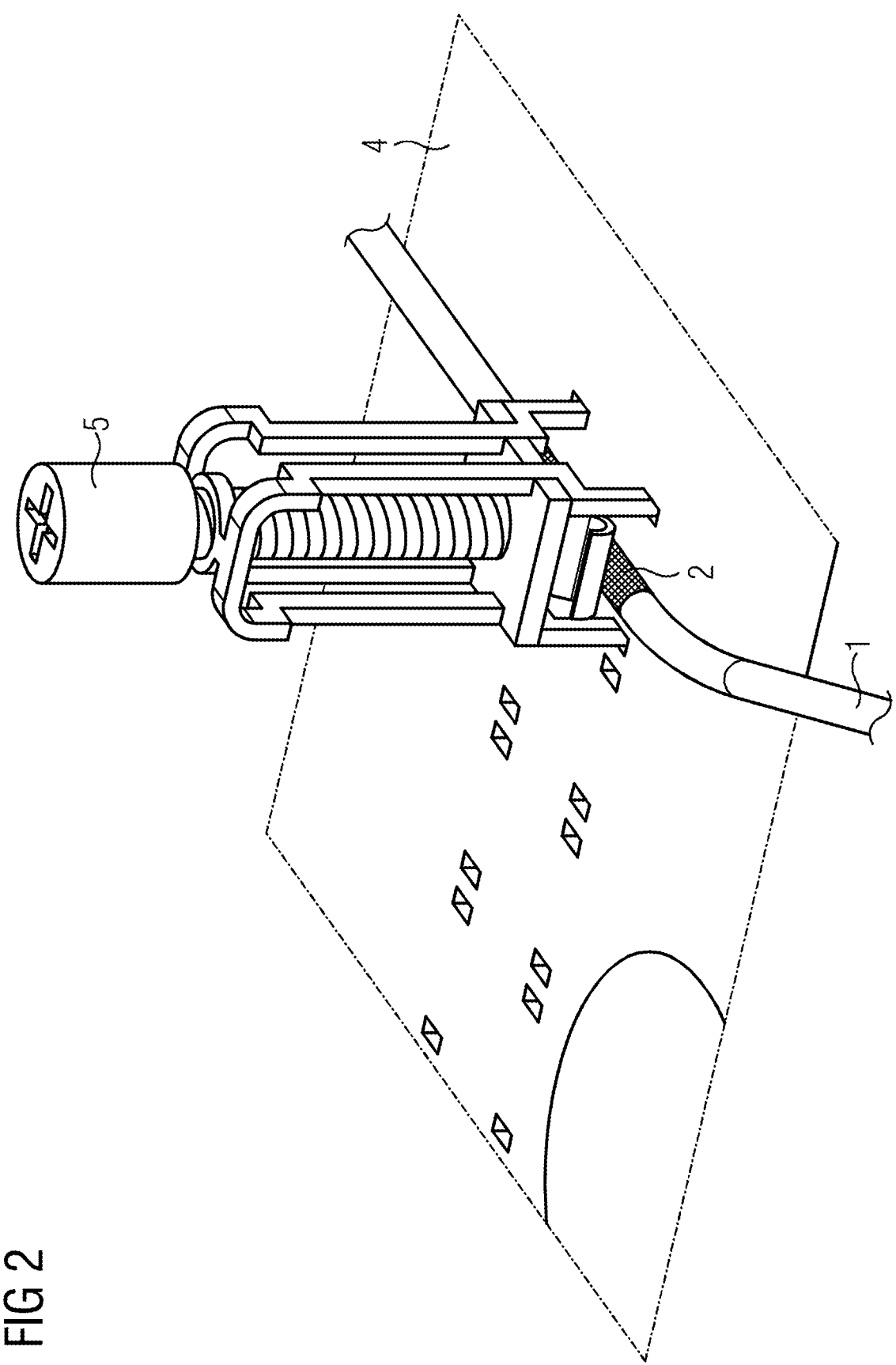
FIG. 2 shows a view of a known screw terminal for contacting a cable shield.

FIGS. 1 and 2 show known apparatuses for electrically contacting shields of electrical cables with a ground potential of a housing 6 of a device. FIG. 1 shows a shield 4 that is arranged in a conducting manner on the housing 6, and has a plurality of electrically conducting spring sheets 3. The plurality of electrically conducting spring sheets 3 are used to fasten cables 1 in a region of an exposed cable shield 2. For this purpose, an insulation of the cables 1 along a section is removed, and the thus exposed cable shield 2 is clamped between the spring sheets 3 (e.g., with a cable tie). A screw terminal 5 into which a cable may likewise be inserted and that is then screwed onto the shield 4 is shown in FIG. 2. With known apparatuses of this type, each cable is to be inserted and fastened individually; for different cable diameters, different fastening elements are frequently to be used.

In accordance with the present embodiments, contact apparatuses 20 are shown in FIGS. 3 to 6. The contact apparatuses 20 of one or more of the present embodiments are brought from a first state, in which a preparation for detachably inserting a plurality of electrical cables is present, into a second state, in which the cables are fixed and an electrical contact is established with the cable shields of the cables, by pressure. With the contact apparatuses 20 of one or more of the present embodiments, a number of cables 1 with different diameters may simultaneously be electrically contacted with the ground potential (e.g., the housing of a device or similar) rapidly and with minimal effort.

Figure 3:
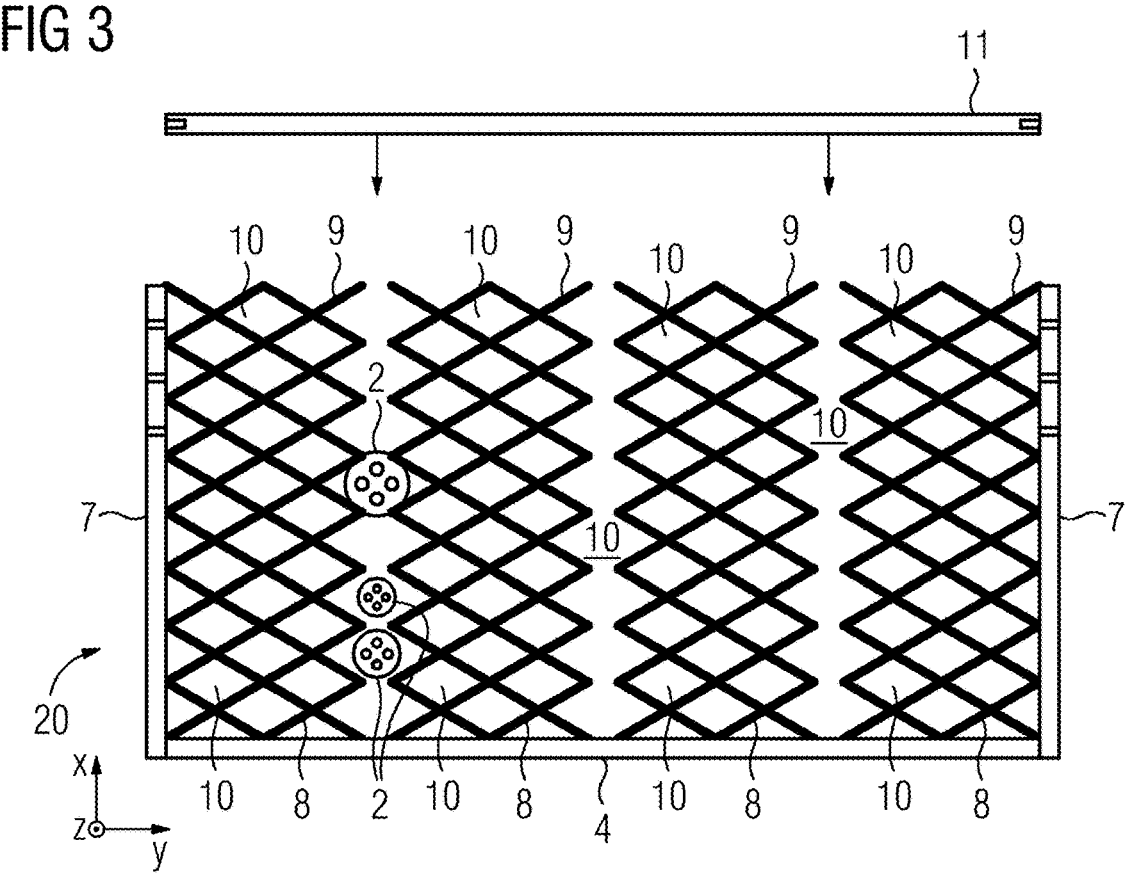
FIG. 3 shows a side view of one embodiment of a contact apparatus in a first state.

In FIG. 3, a contact apparatus 20 that is arranged on a shield 4 of a housing of an electric device is shown in a first state. The contact apparatus 20 includes a number of elements 8 that have a mesh-type structure with a plurality of cutouts 10 and webs 9. The elements may have a two-dimensional mesh structure or also an extension in the z-direction (e.g., a three-dimensional mesh structure). Only one single element may also be available. In the first state shown, cables 1 with a diameter that is different or the same may either be introduced between the elements 8 or (e.g., with just one element) into the cutouts 10. The cables with exposed cable shields 2 may be inserted. In the first state of the contact apparatus 20, the cables 1 are loosely supported in the cutouts or between the elements 8. The elements 8 are configured from an electrically conductive rubber, elastomer, or foam (e.g., from silicon with metal particles). Conductive rubbers or elastomers of this type are known and may be manufactured in any forms. A pressure element 11 is arranged so that, if necessary, the pressure element 11 may exert pressure on the elements 8. One such pressure element 11 may be formed by a plate, for example. A frame 7 may be arranged around the elements 8. The frame 7 and the pressure element 11 may include multiple parts or also form a structural unit.

Figure 4:
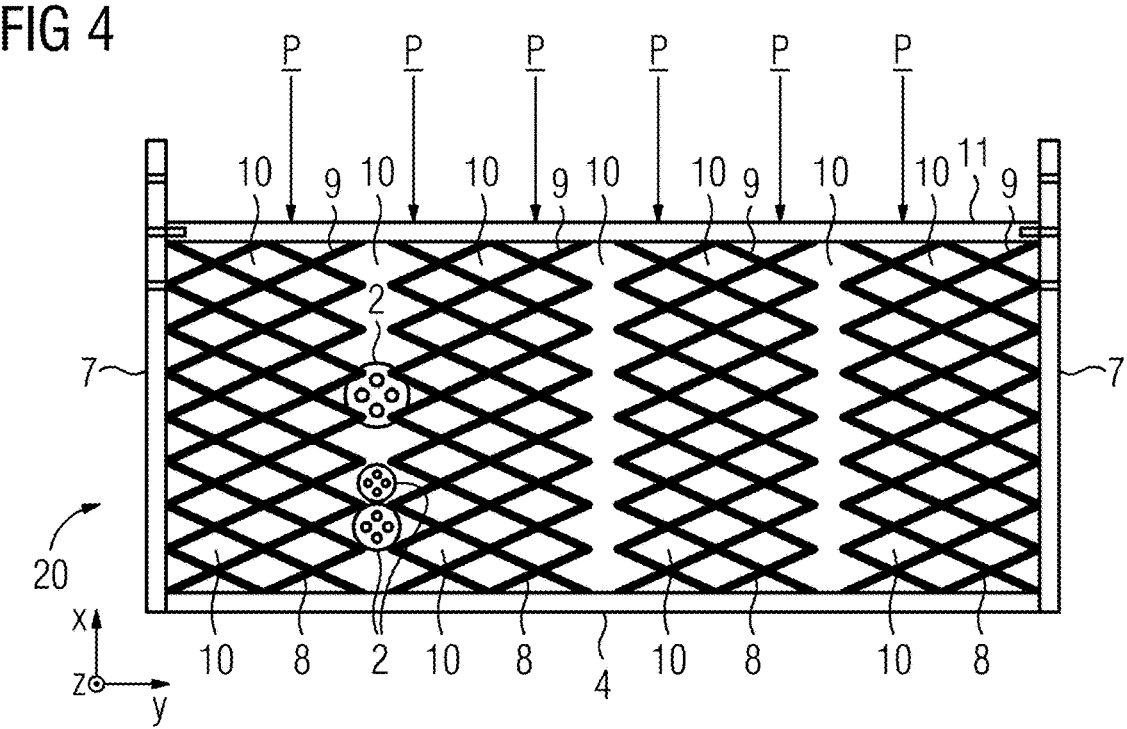
FIG. 4 shows a side view of one embodiment of a contact apparatus in a second state.

In FIG. 4, the contact apparatus is shown in a second state, in which pressure is exerted onto the elements 8 by the pressure element 11. In this way, the elements 8 are pressed together, and the cutouts 10 are reduced in size or the webs 9 are moved closer to one another. As a result, the cables 1 are firmly fixed and electrically contacted. As a result, the elements 8 may, but need not, be pressed against one another. A particularly large bandwidth of cable diameters may be fixed simultaneously by the elasticity of the corresponding materials. The pressure element 11 may be detachably fastened in the pressure-exerting state (e.g., by one or more fastening elements, such as a clip closure, screws, rivets, hooks, or similar). If necessary, when further cables have to be contacted or cables are to be removed, for example, the pressure element may be detached easily, and the pressure may be reduced/removed.

Figure 5:
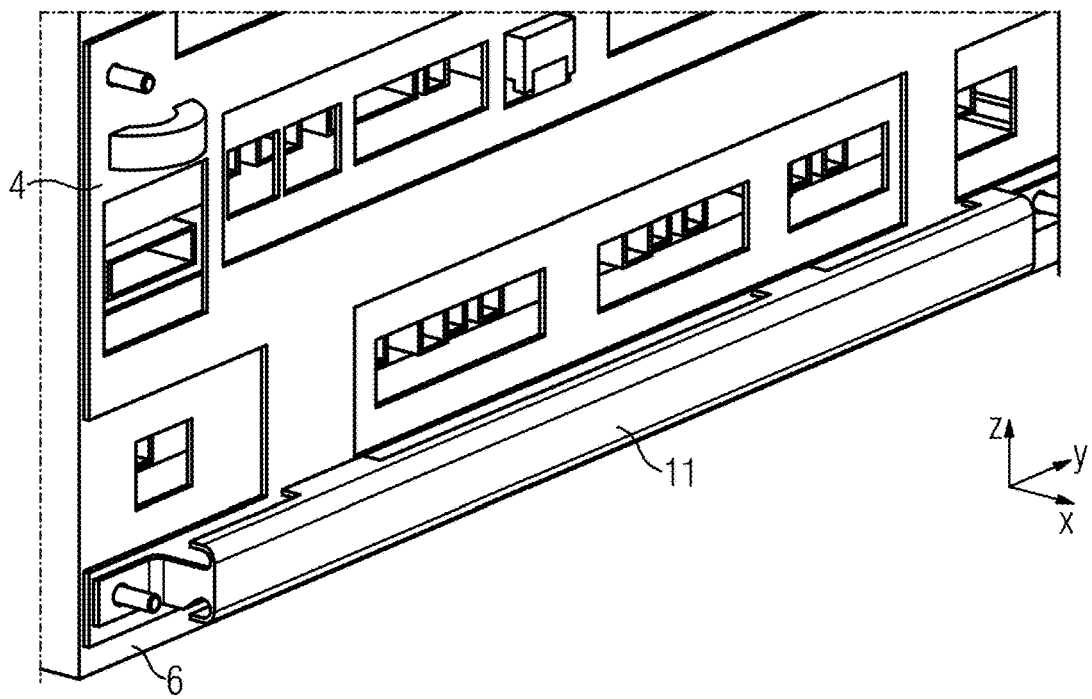
FIG. 5 shows a perspective top view onto a pressure element of another embodiment of a contact apparatus.

FIG. 5 shows a perspective view onto a pressure element 11 arranged on a housing 6 with a shield 4, where the elements 8 lying therebelow between the shield 4 and the pressure element 11 are not visible here.

Figure 6:
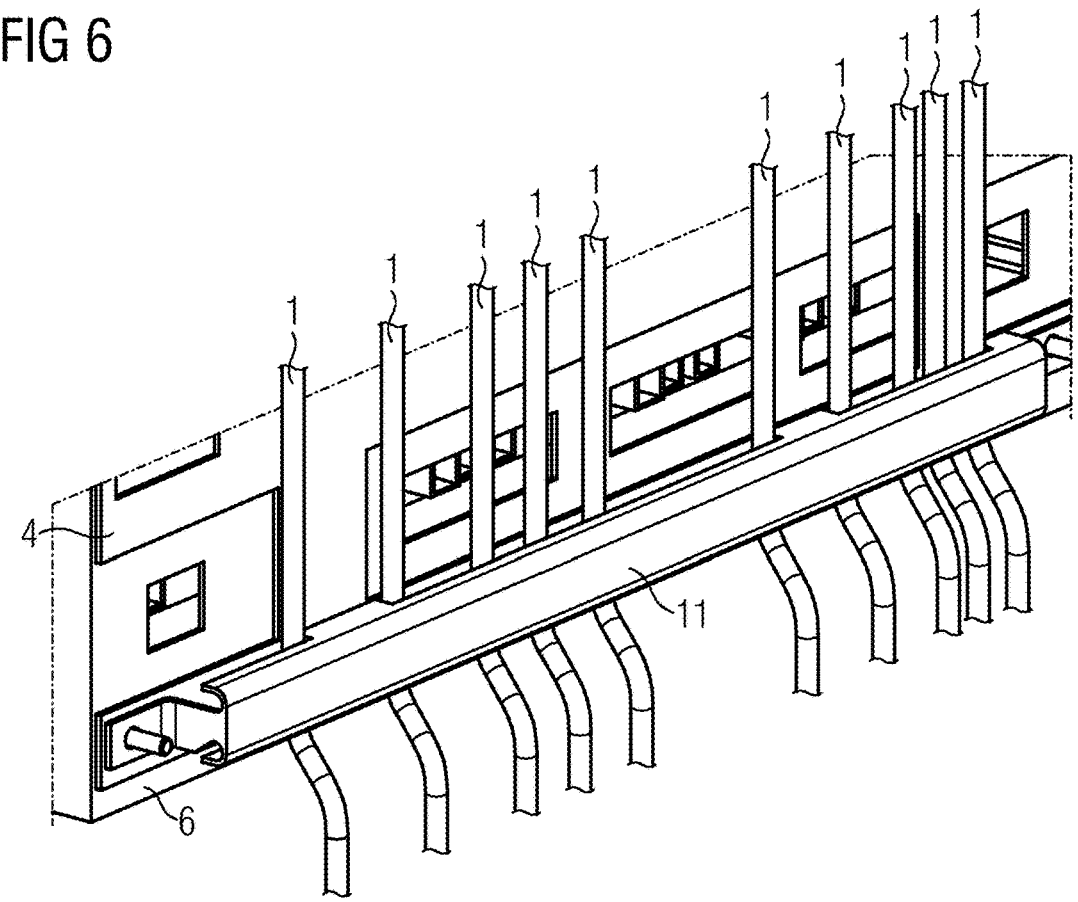
FIG. 6 shows a view according to FIG. 5 with additionally fixed cables.

FIG. 6 shows a similar view to that in FIG. 5 with additionally fixed cables.

Figure 7:
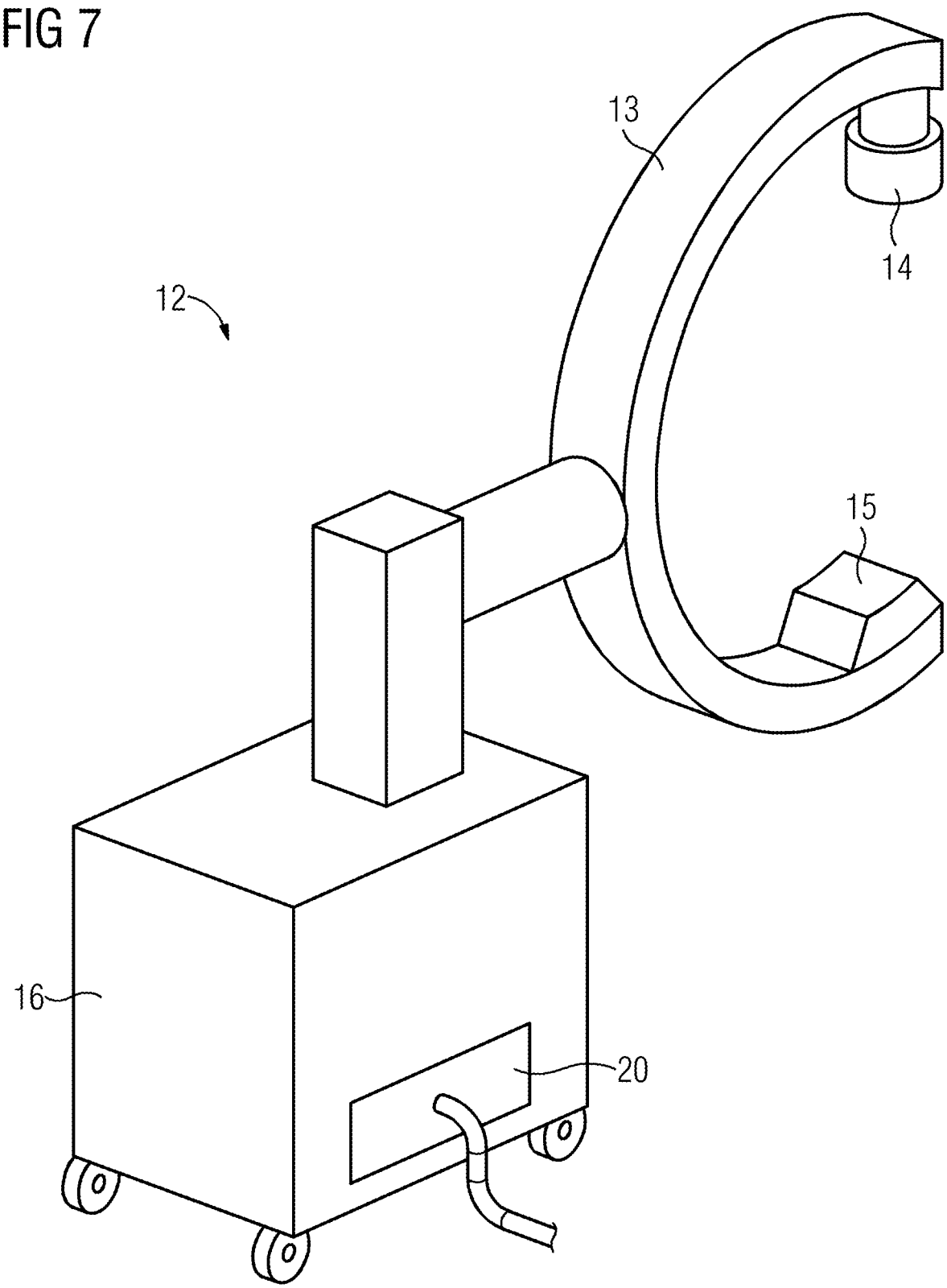
FIG. 7 shows a view of one embodiment of a mobile medical x-ray device with a contact apparatus.

FIG. 7 shows a mobile medical x-ray device 12 with a contact apparatus 20. The mobile x-ray device 12 has a device carriage 16 with a C-arm 13, on which an x-ray source 14 and an x-ray detector 15 are arranged. In order to supply all components of the C-arm 13 with current, a plurality of cables 1 are to be provided. The cables 1 may have different diameters. The contact apparatus 20 may be used in order to be able to contact the cables 1 (e.g., of an assembly) easily and reliably with the ground potential of a conductive housing of an electrical or electronic device or a counterpart provided separately herefor in order to derive interference and compensation currents. Shields may therefore be applied and fixed rapidly. Different diameters of the cables no longer play a role here. Manufacturing costs and service costs may be reduced by rapidly applying the cables.

The present embodiments may be summarized in brief below: a contact apparatus, having at least one conductive, elastic, structured contact unit, which may assume a first state and a second state and may be brought by supplying energy (e.g., pressure) from the first state into the second state, is provided for a particularly rapid and simple electrical contacting with a ground potential of shields of electrical cables with different diameters. The contact unit is embodied so that, in the first state, the contact unit has a preparation for detachably inserting a plurality of electrical cables, and that in the second state, the contact unit fixes the cables and establishes an electrical contact with the cable shields of the cables.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A contact apparatus for electrically contacting cable shields of electrical cables with a ground potential, the contact apparatus comprising:

at least one contact unit that is conductive, elastic, and structured, and is operable to assume a first state and a second state, the at least one contact unit being operable to be brought from the first state into the second state by supplying energy, wherein the at least one contact unit is configured so that:
in the first state, the at least one contact unit has a preparation for detachably inserting a plurality of electrical cables; and
in the second state, the at least one contact unit fixes the electrical cables and establishes an electrical contact with the cable shields of the electrical cables, and
wherein the at least one contact unit is operable to move from the first state into the second state when pressure is exerted.

2. The contact apparatus of claim 1, wherein the at least one contact unit is operable to move from the second state into the first state when the pressure is taken away.

3. The contact apparatus of claim 1, wherein the at least one contact unit is formed at least partially from a conductive rubber or elastomer.

4. The contact apparatus of claim 1, wherein the at least one contact unit has at least one element that has cutouts and webs.

5. The contact apparatus of claim 4, wherein the at least one element has a three-dimensional, mesh-type structure.

6. The contact apparatus of claim 4, wherein the at least one element includes at least two elements that are arranged so that in the first state, the at least two elements are at a distance from one another, and in the second state, the at least two elements are in contact with one another.

7. The contact apparatus of claim 1, wherein in the second state, the at least one contact unit electrically connects the cable shields to the ground potential of an electrical device.

8. The contact apparatus of claim 1, further comprising a frame with a pressure element configured to exert pressure onto the at least one contact unit.

9. The contact apparatus of claim 8, wherein the pressure element includes a plate.

10. A medical device comprising:
a contact apparatus for electrically contacting cable shields of electrical cables with a ground potential, the contact apparatus comprising:
at least one contact unit that is conductive, elastic, and structured, and is operable to assume a first state and a second state, the at least one contact unit being operable to be brought from the first state into the second state by supplying energy,
wherein the at least one contact unit is configured so that:
in the first state, the at least one contact unit has a preparation for detachably inserting a plurality of electrical cables; and
in the second state, the at least one contact unit fixes the electrical cables and establishes an electrical contact with the cable shields of the electrical cables, and
wherein the at least one contact unit is operable to move from the second state into the first state when pressure is taken away.

11. The medical device of claim 10, wherein the medical device is configured as a mobile x-ray device with a C-arm for holding an x-ray detector and an x-ray source, and
wherein the cables are configured to supply power to components of the C-arm.

12. The medical device of claim 10, wherein the at least one contact unit is operable to move from the first state into the second state when pressure is exerted.

13. The medical device of claim 10, wherein the at least one contact unit is formed at least partially from a conductive rubber or elastomer.

14. The medical device of claim 10, wherein the at least one contact unit has at least one element that has cutouts and webs.

15. The medical device of claim 14, wherein the at least one element has a three-dimensional, mesh-type structure.

16. The medical device of claim 14, wherein the at least one element includes at least two elements that are arranged so that in the first state, the at least two elements are at a distance from one another, and in the second state, the at least two elements are in contact with one another.

17. The medical device of claim 10, wherein in the second state, the at least one contact unit electrically connects the cable shields to the ground potential of an electrical device.

18. A contact apparatus for electrically contacting cable shields of electrical cables with a ground potential, the contact apparatus comprising:
at least one contact unit that is conductive, elastic, and structured, and is operable to assume a first state and a second state, the at least one contact unit being operable to be brought from the first state into the second state by supplying energy;
a frame with a pressure element configured to exert pressure onto the at least one contact unit,
wherein the pressure element includes a plate, and
wherein the at least one contact unit is configured so that:
in the first state, the at least one contact unit has a preparation for detachably inserting a plurality of electrical cables; and
in the second state, the at least one contact unit fixes the electrical cables and establishes an electrical contact with the cable shields of the electrical cables.

* * * * *